United States Patent
Allier et al.

(10) Patent No.: US 9,568,433 B2
(45) Date of Patent: Feb. 14, 2017

(54) SYSTEM AND METHOD FOR OPTICAL DETECTION INCLUDING A COMPOSITION FOR THE OPTICAL DETECTION OF PARTICLES, COMPRISING WATER, THE PARTICLES, A SURFACTANT AND A HYDROPHILIC POLYMER

(71) Applicant: Commissariat à l'énergie atomique et aux énergies alternatives, Paris (FR)

(72) Inventors: Cédric Allier, Grenoble (FR); Yves Hennequin, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 207 days.

(21) Appl. No.: 14/414,239

(22) PCT Filed: Jul. 11, 2013

(86) PCT No.: PCT/EP2013/064669
§ 371 (c)(1),
(2) Date: Jan. 12, 2015

(87) PCT Pub. No.: WO2014/009462
PCT Pub. Date: Jan. 16, 2014

(65) Prior Publication Data
US 2015/0185163 A1  Jul. 2, 2015

(30) Foreign Application Priority Data
Jul. 12, 2012  (FR) ..................... 12 56736

(51) Int. Cl.
*G01N 21/85* (2006.01)
*C08L 71/02* (2006.01)
(Continued)

(52) U.S. Cl.
CPC ............... *G01N 21/85* (2013.01); *C08K 5/103* (2013.01); *C08L 71/02* (2013.01);
(Continued)

(58) Field of Classification Search
CPC ................ G01N 21/85; G01N 15/1434; G01N 2015/1454; G01N 2015/1006; C08L 71/02; C08K 5/103
(Continued)

(56) References Cited

U.S. PATENT DOCUMENTS 4,148,869 A    4/1979  Deaton
6,312,960 B1 * 11/2001  Balch .................. B01J 19/0046
                                                              422/105
(Continued)

FOREIGN PATENT DOCUMENTS

WO    WO 2010/051607        5/2010

OTHER PUBLICATIONS

International Search Report for PCT/EP2013/064669 dated Apr. 8, 2014.

*Primary Examiner* — Seung C Sohn
(74) *Attorney, Agent, or Firm* — B. Aaron Schulman, Esq.; Stites & Harbison, PLLC (57) ABSTRACT

A system for detecting optical particles comprises a transparent slide, a composition arranged on the slide, a light source able to light the composition and the slide, and a device for acquiring at least one image of the composition lit by the light source, the transparent slide being positioned between the light source and the acquisition device. The composition comprises water, the particles, a surfactant and a hydrophilic polymer, the particles having a diameter preferably smaller than 10 pm, still more preferably smaller than 1 pm, the surfactant having a concentration preferably at least equal to the critical micellar concentration, the
(Continued)

hydrophilic polymer having a boiling temperature higher than that of water.

21 Claims, 6 Drawing Sheets

(51) Int. Cl.
*C08K 5/103* (2006.01)
*G01N 15/14* (2006.01)
*G01N 15/10* (2006.01)

(52) U.S. Cl.
CPC . *G01N 15/1434* (2013.01); *G01N 2015/1006* (2013.01); *G01N 2015/1454* (2013.01)

(58) Field of Classification Search
USPC .................................................. 250/208.2
See application file for complete search history.

(56) References Cited

U.S. PATENT DOCUMENTS 8,605,265 B2 * 12/2013 Allier ................. G01N 15/1475
356/36
2011/0228256 A1    9/2011 Allier

* cited by examiner

SYSTEM AND METHOD FOR OPTICAL DETECTION INCLUDING A COMPOSITION FOR THE OPTICAL DETECTION OF PARTICLES, COMPRISING WATER, THE PARTICLES, A SURFACTANT AND A HYDROPHILIC POLYMER

BACKGROUND OF THE INVENTION

The invention relates to a detection system for detecting optical particles, the system comprising a transparent slide, a composition arranged on the slide, a light source able to light the composition and the slide, and a device for acquiring at least one image of the composition lit by the light source, the transparent slide being positioned between the light source and the acquisition device.

The optical particle detection composition comprises water, the particles and a surfactant, the particles having a diameter preferably smaller than 10 μm and in particular a diameter smaller than 1 μm, the surfactant having a concentration preferably at least equal to the critical micellar concentration (CMC).

The invention also relates to a method for detecting optical particles using such an optical detection system.

The invention in particular applies to the detection of micrometric and sub-micrometric particles, in particular biological particles, such as cells, bacteria or viruses. The invention also applies to the detection of particles in the form of microbeads.

A detection system of the aforementioned type is known from document WO 2011/045360 A1. The composition comprises micrometric or sub-micrometric particles or organisms, water and a wetting agent, such as polyoxyethylene 20 sorbitan monolaurate, also known under the commercial name TWEEN 20.

This composition is deposited in the form of a drop on the transparent slide, and images of the drop are acquired during its evaporation. When the drop evaporates, the formation of a film on the surface of the particle is observed, and that residual film, covering the particle, serves as a micro-lens, which makes it possible to improve the detection of the particle.

However, such a detection system does not allow easy detection of particles with a size smaller than a micrometer. In fact, below that size, the signal-to-noise ratio decreases.

SUMMARY OF THE INVENTION

The aim of the invention is therefore to propose a system for optical particle detection making it possible to detect particles having a diameter smaller than a micrometer.

To that end, the invention relates to a system for detecting optical particles, comprising a transparent slide, a composition arranged on the transparent slide, a light source able to light the composition and the slide, and a device for acquiring at least one image of the composition lit by the light source, the transparent slide being positioned between the light source and the acquisition device, in which the composition comprises water, particles, a surfactant and a hydrophilic polymer, the particles having a diameter preferably smaller than 10 μm, still more preferably smaller than 1 μm, the surfactant having a concentration preferably at least equal to the critical micellar concentration, the hydrophilic polymer having a boiling temperature higher than that of water.

According to other advantageous aspects of the invention, the optical detection system comprises one or more of the following features, considered alone or according to all technically possible combinations:

the polymer is a polyethylene glycol defined by the following formula:

where n represents the number of oxyethylene patterns of the polymer;

the number n of oxyethylene patterns is an integer comprised between 2 and 180, preferably comprised between 4 and 16, still more preferably equal to 13;

the number n of oxyethylene patterns is equal to 13, and the hydrophilic polymer has a weight concentration comprised between 0.2% and 0.8%, preferably comprised between 0.4% and 0.6%; and the surfactant comprises polyoxyethylene 20 sorbitan monolaurate.

The invention also relates to a method for detecting optical particles, the particles having a diameter preferably smaller than 10 μm, still more preferably smaller than 1 μm, the method comprising the following steps:

arranging, on a transparent slide, a composition comprising water, the particles and a surfactant, the surfactant having a concentration preferably at least equal to the critical micellar concentration, acquiring at least one image of the particles using an optical detection system, wherein the composition further comprises a hydrophilic polymer, the hydrophilic polymer having a boiling temperature higher than that of water.

According to other advantageous aspects of the invention, the detection method comprises one or more of the following features, considered alone or according to all technically possible combinations:

the polymer is a polyethylene glycol defined by the following formula:

where n represents the number of oxyethylene patterns of the polymer, the number n of oxyethylene patterns being an integer, preferably comprised between 2 and 180, still more preferably comprised between 4 and 16, still more preferably equal to 13;

the optical detection system comprises a microscope having a main object plane perpendicular to a vertical direction, and during the acquisition step, a first image is acquired for a first focus above the main object plane of the microscope, a second image is acquired for a second focus below the main object plane of the microscope, and the second image is subtracted from the first image; and the first focus and the second focus are substantially symmetrical to each other relative to the main object plane of the microscope.

BRIEF DESCRIPTION OF THE DRAWINGS

The features and advantages of the invention will appear upon reading the following description, provided solely as a non-limiting example, and done in reference to the appended drawings, in which.

DETAILED DESCRIPTION OF PREFERRED EMBODIMENTS

Figure 1:
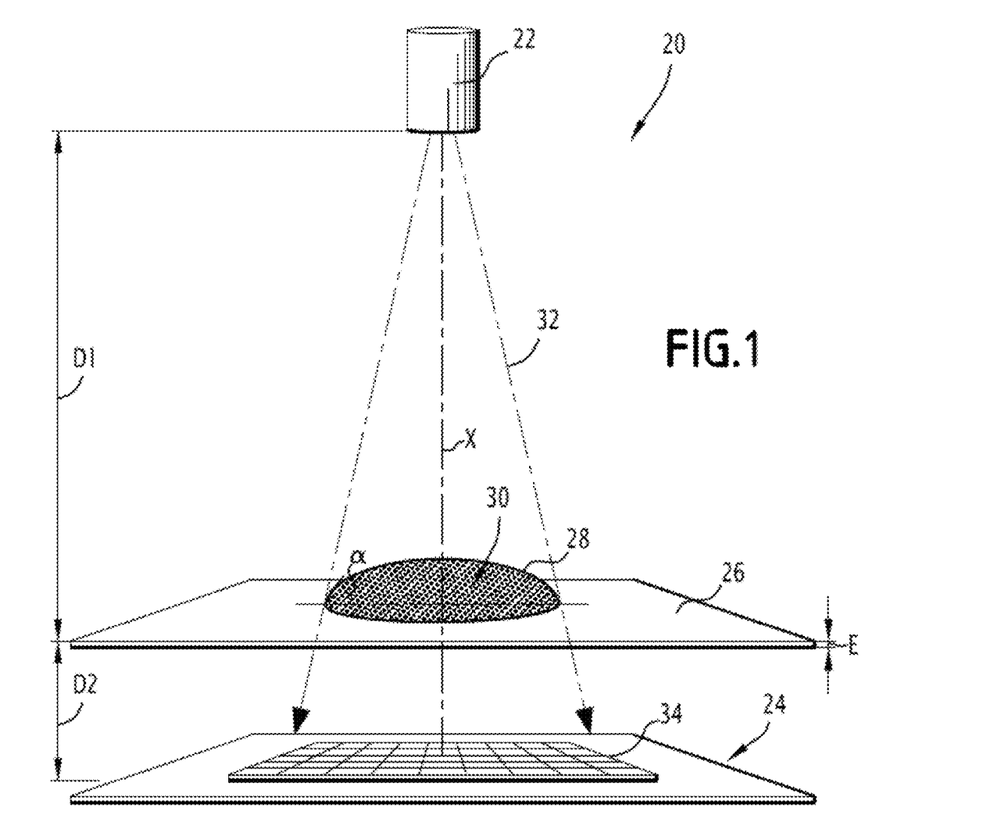
FIG. 1 is a diagrammatic illustration of an optical particle detection system, according to a first embodiment of the invention, the detection system comprising a light source, a transparent slide on which a composition is arranged, and a device for acquiring images of the lit composition.

In FIG. 1, an optical detection system 20 comprises a light source 22, an image acquisition device 24, a transparent slide 26 and a composition 28 arranged on the slide 26, the composition 28 comprising particles to be detected 30.

The detection system 20 is designed to detect the particles 30, the latter having a diameter preferably smaller than 1 μm, during the evaporation of the composition 28, the composition 28 being deposited in the form of a drop on the transparent slide 26.

The light source 22 is able to emit a light beam 32 in a longitudinal direction X, in order to light the composition 28 arranged on the transparent slide 26.

The light source 22 is arranged at a first distance D1 from the transparent slide 26 in the longitudinal direction X. The first distance D1 preferably has a value comprised between 1 cm and 30 cm, for example equal to 10 cm.

In the example embodiment of FIG. 1, the light source 22 is a periodic source. The spatial coherence of the light source 22 is additionally improved, for example by coupling it with a pinhole, with a diameter comprised between 50 μm and 500 μm, placed in contact with the source 22.

The light source 22 is for example a light-emitting diode (LED), monochromatic and having small enough dimensions to be considered spatially coherent, the diameter of the light-emitting diode being smaller than one tenth of the first distance D1 separating the light-emitting diode from the slide 26. The light-emitting diode of the light source 22 for example has a transmission wavelength equal 555 nm and a power equal to 1.7 W.

Alternatively, the light source 22 is a spatially or temporally coherent light source, such as a laser diode (LD) or a Vertical Cavity Surface Emitting Laser (VSCEL).

The image acquisition device 24 comprises a matrix photodetector 34 comprising a plurality of pixels, not shown. Each pixel of the photodetector 34 has dimensions smaller than or equal to 10 μm, or even 4 μm. Each pixel is for example in the shape of a square with each side having a value smaller than or equal to 10 μm, or even 4 μm. Alternatively, each pixel is in the shape of a square with each side measuring 2.2 μm.

The image acquisition device 24 is positioned at a second distance D2 from the transparent slide 26 in the longitudinal direction X. The second distance D2 has a value smaller than 1 cm, and preferably comprised between 100 μm and 2 mm.

In the example embodiment of FIG. 1, the second distance D2 is equal to 500 μm. Favoring a short distance between the acquisition device 24 and the transparent slide 26 makes it possible to limit the interference phenomena between different diffraction patterns when the composition 28 is lit.

The image acquisition device 24 is able to acquire images of the radiation transmitted by the slide 26 on which the composition 28 lit by the light beam 32 is arranged. "Transmitted radiation" refers to the radiation passing through the composition 28 and the slide 26, such that the acquisition device 24 and the light source 22 are situated on either side of the transparent slide 26 and the composition 28.

The transparent slide 26 is positioned between the light source 22 and the acquisition device 24, and is substantially perpendicular to the longitudinal direction X.

The transparent slide 26 has a thickness E in the longitudinal direction X. The thickness E for example has a value comprised between 10 μm and 100 μm, preferably comprised between 20 μm and 50 μm.

The slide 26 is preferably hydrophilic, so that the contact angle α, visible in FIG. 1, between the composition 28 and the slide 26 has a small value. The value of the contact angle α obtained between the hydrophilic slide 26 and the composition 28 is smaller than 20°, preferably smaller than 10°, still more preferably approximately one degree.

The hydrophilic nature of the slide 26 is for example typical obtained by preparing the slide 26 according to the following steps. The first preparation step involves sonication in soapy water for approximately ten minutes. The soapy water for example comprises water and dishwashing liquid, the water preferably being type 1 pure water according to standard ISO 3696, also known under the commercial name Mili-Q. The second step involves rinsing with water, such as Mili-Q water, acetone and isopropanol. The third step is a drying step, for example drying with nitrogen, and the fourth step involves passage through oxygen plasma for more than 15 seconds, preferably approximately 30 seconds.

The composition 28 comprises the particles to be detected 30 and a solution, the solution comprising water, a surfactant and a hydrophilic polymer. In other words, the composition 28 is a dispersion of particles to be detected 30 in an aqueous solution comprising water, the surfactant and the hydrophilic polymer.

In the described example embodiment, the solution of the composition 28 is made up of water, surfactant and hydrophilic polymer. The composition 28 is then made up of the particles to be detected 30, water, surfactant and hydrophilic polymer.

The hydrophilic polymer has a boiling temperature higher than that of water. The hydrophilic polymer is for example a polyethylene glycol defined by the following formula:

where n represents the number of oxyethylene patterns of the polymer.

The number n of oxyethylene patterns is an integer, preferably comprised between 2 and 180, still more preferably comprised between 4 and 16, still more preferably equal to 13.

As will be described in more detail below, the number n of patterns is for example equal to 2, and the polymer is then called diethylene glycol, also denoted DiEG.

Alternatively, the number n of oxyethylene patterns is equal to 13, and the hydrophilic polymer is called polyethylene glycol 600, also denoted PEG 600, the PEG 600 having a molecular weight of approximately 600 g/mol.

When the number n of oxyethylene patterns is equal to 13, the hydrophilic polymer, i.e., the PEG 600, has a weight concentration preferably comprised between 0.2% and 0.8%, still more preferably comprised between 0.4% and 0.6%.

Also alternatively, the number n of oxyethylene patterns is equal to 180, and the hydrophilic polymer is called polyethylene glycol 8000, also denoted PEG 8000, the PEG 8000 having a molecular weight substantially equal to 8000 g/mol.

The surfactant, also called surface active agent, has a concentration preferably at least equal to the critical micellar concentration (CMC). The surfactant for example comprises polyoxyethylene 20 sorbitan monolaurate, also known under the commercial name TWEEN20.

Alternatively, the surfactant comprises a copolymer of polyoxyethylene and polyoxyethylene, such as poloxamer, for example that known under the commercial name PLURONIC F-68. Also alternatively, the surfactant comprises sodium dodecyl sulfate, also called SDS.

The particles to be detected 30 are, for example, biological particles, i.e., cells (for example red blood cells, white blood cells or platelets), cellular components (for example, mitochondria), bacteria, viruses or any other molecule or aggregates of molecules, in particular protein aggregates.

Alternatively, the particles to be detected 30 are microbeads.

The particles to be detected 30 have a diameter preferably smaller than 1 µm, the diameter of the particles 30 for example being comprised between 50 nm and 1 µm, still more preferably comprised between 10 nm and 1 µm.

The light beam 32 is able to light the composition 28 positioned on the transparent slide 26 directly.

The matrix photodetector 34 is a two-dimensional image sensor, i.e., in a plane perpendicular to the longitudinal axis X. The matrix photodetector 34 is a pixelated image sensor, for example a CMOS (Complementary Metal Oxide Semiconductor) sensor.

Alternatively, the matrix photodetector 34 is a CCD (Charged-Coupled Device) sensor.

The images acquired by the matrix photodetector 34 are formed by the radiation transmitted directly by the lit composition 28, in the absence of a magnifying lens positioned between the transparent slide 26 and the matrix photodetector 34. However, this does not rule out the presence of micro-lenses, each being coupled to a corresponding pixel of the sensor, those micro-lenses allowing better collection of the signal. The matrix photodetector 34 is also called a lens-free imaging device, and can form an image of the composition 28, while being placed at a small distance therefrom. A small distance refers to a distance shorter than 1 cm, the second distance D2 for example being approximately 500 µm.

The optical particle detection method 30 will now be described.

The initial step consists of arranging the composition 28, comprising the water, surfactant, hydrophilic polymer and particles 30, on the transparent slide 26. The composition 28 is in the form of a drop positioned on the slide 26. The volume of the drop is for example comprised between 1 µL and 20 µL.

Successive images of the drop containing the particles 30 are then acquired using the optical detection system 20. During the evaporation of the drop, the formation of a wetting film is then observed covering the particles 30, the wetting film having a very small thickness, such as a thickness comprised between 10 nm and 5 µm.

When the composition 28 is lit by the light source 22 under these conditions, the wetting film then acts as one or more micro-lenses formed above the particles 30, which makes it possible to improve the detection of those particles.

The addition of the hydrophilic polymer in the composition 28 makes it possible to prolong the duration during which the wetting film remains in contact with the particles 30 during the evaporation of the drop. The hydrophilic polymer makes it possible to extend the appearance duration of the film, while maintaining correct spreading of the drop on the slide 26. The contact angle α obtained between the slide 26 and the composition 28 in fact has a value below 20°, preferably below 1° and 10°, still more preferably approximately one degree.

The hydrophilic polymer also causes a decrease in the thickness of the wetting film obtained during the evaporation of the drop, which makes it possible to detect particles 30 with a smaller size, while keeping a good signal-to-noise ratio. Indeed, if the thickness of the wetting film is too great relative to the particles 30 one wishes to detect, then the signal-to-noise ratio decreases.

When the surfactant has a concentration at least equal to the critical micellar concentration, the drop spreads even better, while having a sufficient evaporation speed to allow the film to form.

Figure 2:
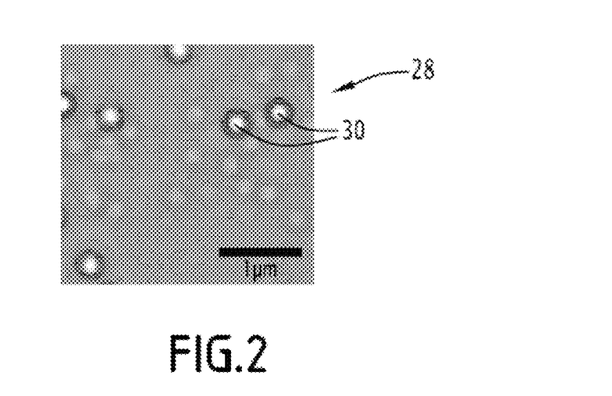
FIG. 2 is an acquired image, using the detection system of FIG. 1, of the composition in the form of a drop during its evaporation, the composition comprising a hydrophilic polymer, 200 nm beads and impurities of approximately 1 μm.

The detection system 20 according to the invention makes it possible to detect particles 30 having a very small diameter, for example particles having a diameter of 200 nm as illustrated in the image of FIG. 2.

In the example embodiment of FIG. 2, the hydrophilic polymer is PEG 600 with a weight concentration equal to 0.4%.

FIGS. 3 to 17 illustrate a second embodiment of the invention, in which the elements similar to the first embodiment, previously described, are identified using identical references, and are not described again.

Figures 3, 4:
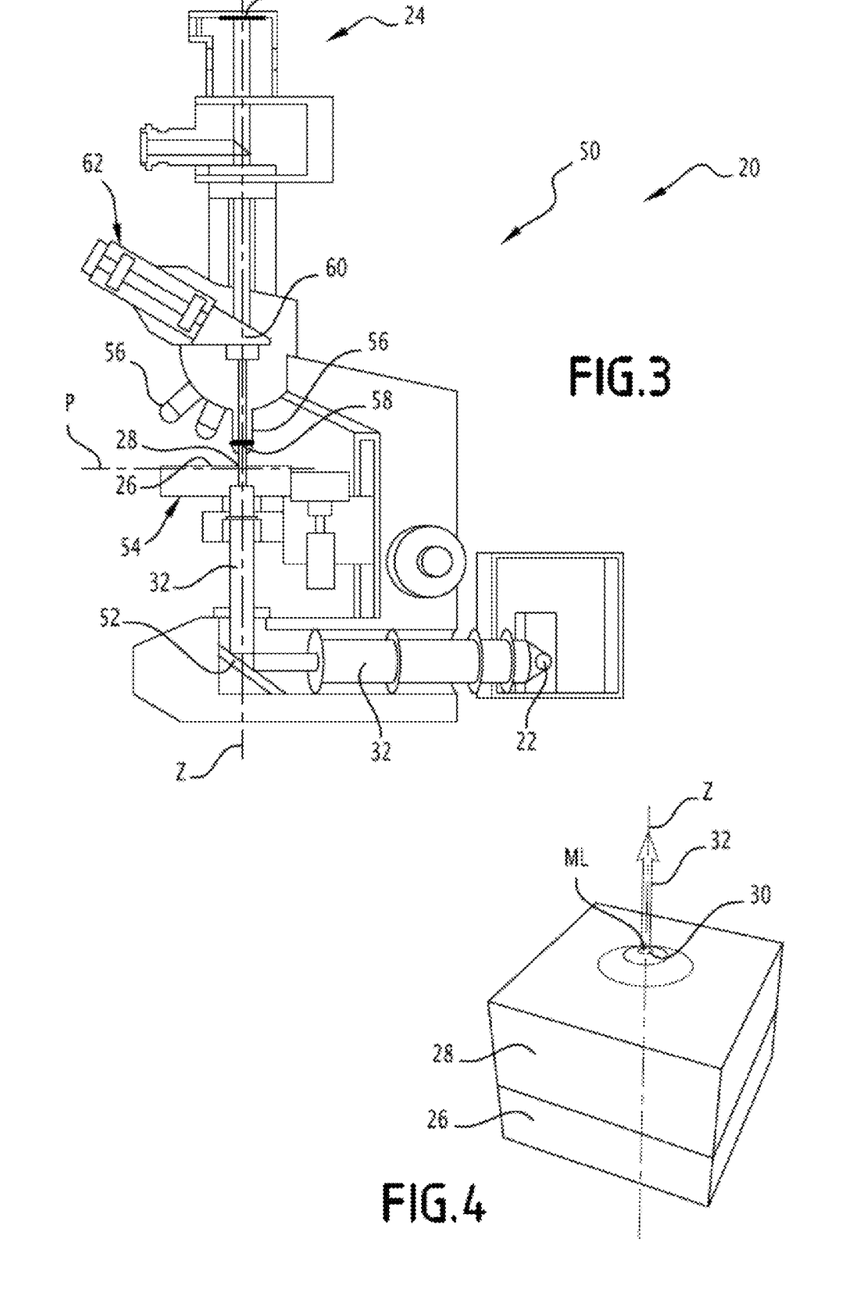
FIG. 3 is a diagrammatic illustration of the optical detection system, according to a second embodiment of the invention, the detection system comprising a microscope.
FIG. 4 is a diagrammatic illustration of the path of the light through the transparent slide and the composition with the detection system of FIG. 3, FIGS. 5 and 6 each show an image acquired using the detection system of FIG. 3 for a first focus, a second focus, respectively, relative to a main object plane of the microscope, when the polymer contained in the composition is polyethylene glycol with a number of oxyethylene patterns equal to 13, also called PEG 600.

According to the second embodiment, the optical detection system 20 comprises a microscope 50 having a main object plane P perpendicular to a vertical direction Z.

The microscope 50 comprises a mirror 52 able to reflect the light beam 32, coming from the light source 22, toward the transparent slide 26 in the vertical direction Z. The microscope 50 comprises a support plate 54 on which the transparent slide 26 is positioned.

In the example embodiment of FIG. 3, the microscope 50 comprises three objectives 56, each objective 56 comprising a first lens 58, also called object lens.

Additionally, the microscope 50 comprises a separating device 60, such as a prism, and an eyepiece 62, the separating device 60 being able to orient the radiation transmitted through the transparent slide 26 and the composition 28, on the one hand toward the eyepiece 62, and on the other hand toward the acquisition device 24 comprising the matrix photodetector 34.

The light source 22 is known in itself and adapted to the microscope 50.

The acquisition device 24 is similar to that of the first body, and comprises the matrix photodetector 34, such as a CMOS sensor or a CCD sensor.

The transparent slide 26 is identical to that of the first body, and prepared similarly.

The composition 28 is identical to any one of those described for the first embodiment.

Figure 5:
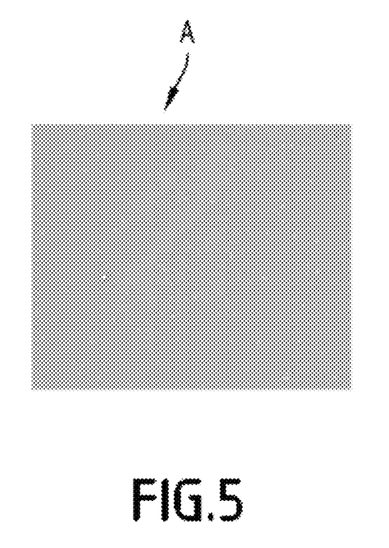
Figure 6:
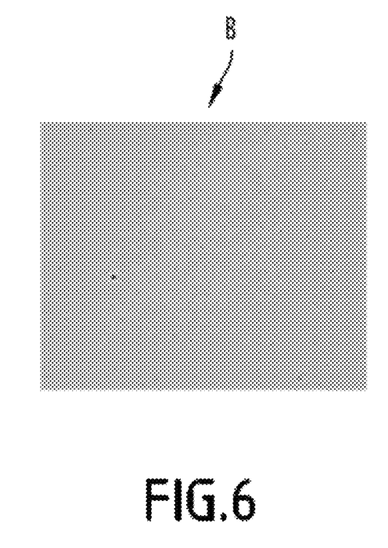
Figure 7:
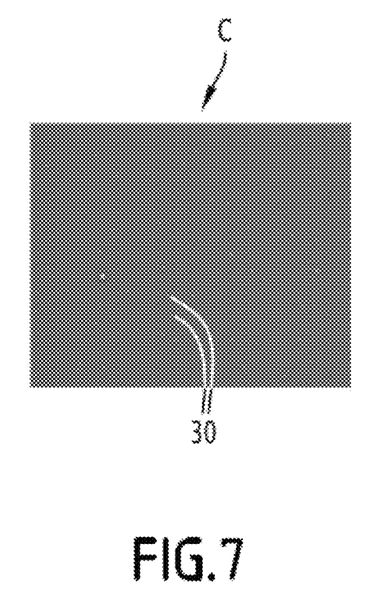
FIG. 7 is an image corresponding to the subtraction of the images of FIGS. 5 and 6.
Figure 10:
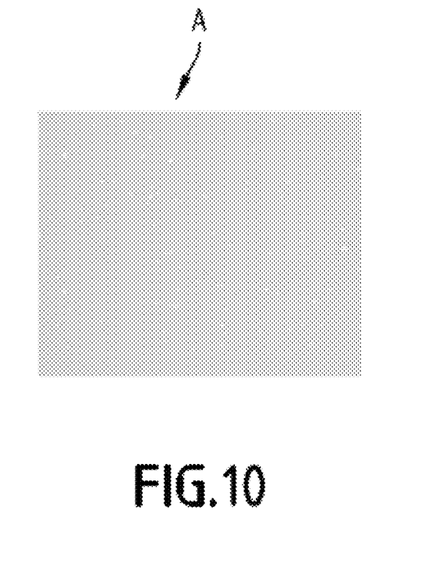
FIGS. 10 to 12 are views similar to those of FIGS. 5 to 7, when the polymer contained in the composition is diethylene glycol, the number of oxyethylene patterns then being equal to 2.
Figure 11:
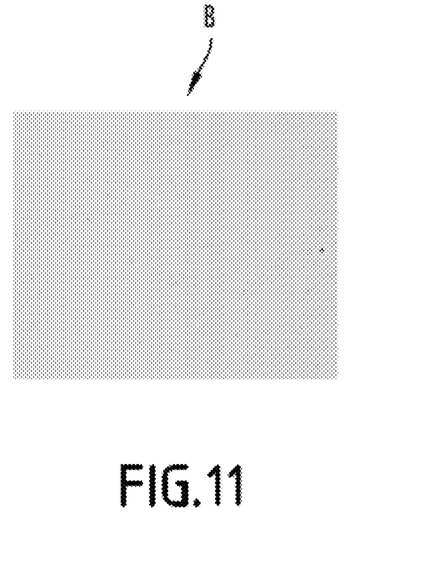
Figure 12:
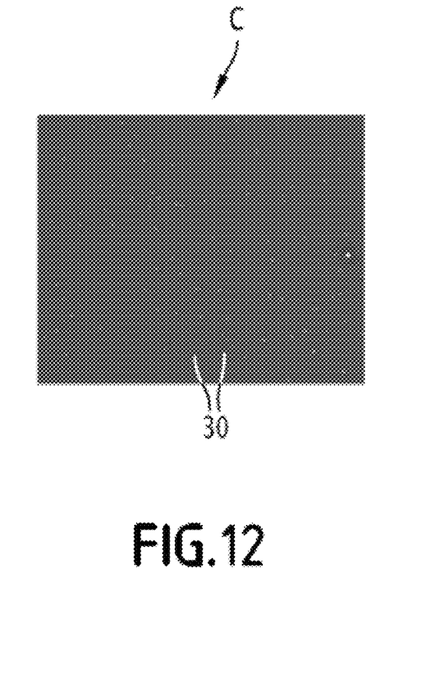
Figure 14:
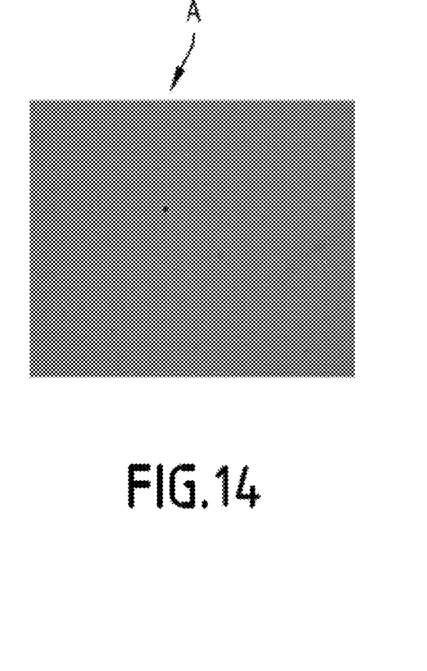
Figure 15:
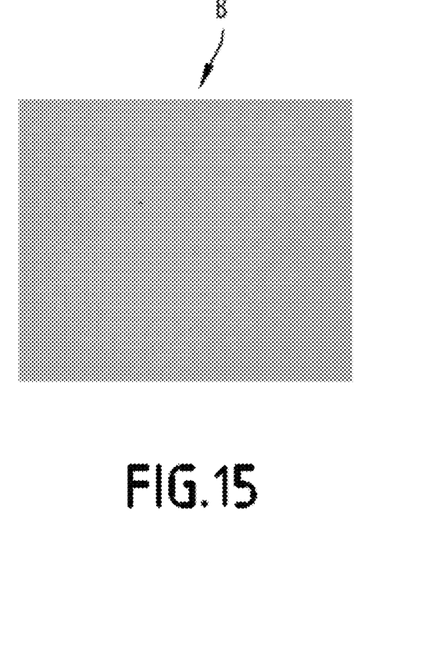
Figure 16:
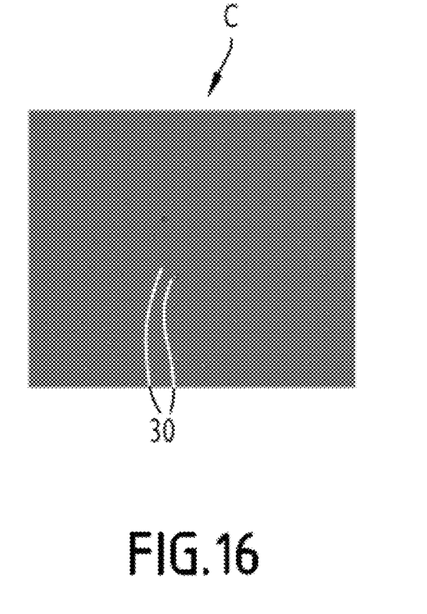

According to the second embodiment, during the acquisition step, a first image A, shown in FIGS. 5, 10 and 14, is acquired for a first focus above the main object plane P of the microscope 50. The observed particles then appear in the form of light points (pixels with a higher gray level than the background). A second image B, shown in FIGS. 6, 11 and 15, is acquired for a second focus below the main object plane P of the microscope 50. The observed particles then appear in the form of dark points (pixels with lower gray levels then the background) and a resulting image C, shown in FIGS. 7, 12 and 16, is obtained by subtracting the second image B from the first image A, in order to improve the acquisition result.

The first focus and the second focus are for example substantially symmetrical to each other relative to the main object plane P of the microscope 50. The first focus is at a first altitude $+Z_0$, the second focus is at a second altitude $-Z_0$, with the convention that the main object plane of the microscope 50 is at the zero altitude.

Identically to the first embodiment, the formation of a wetting film is observed covering the particles 30 during the evaporation of the drop of the composition 28, the wetting film covering the particle 30 then acting as a micro-lens ML, as shown in FIG. 4.

The optical particle detection method 30 according to the second embodiment is similar to that of the first embodiment previously described.

In the example embodiment of FIGS. 5 to 17, the particles 30 have a diameter substantially equal to 200 nm.

In the example embodiment of FIGS. 5 to 7, the hydrophilic polymer is PEG 600, and the number n of oxyethylene patterns is then equal to 13.

Figure 8:
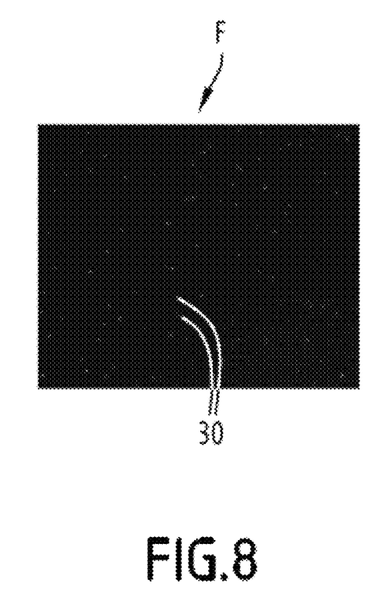
FIG. 8 is a reference image of the same particles obtained by molecular fluorescence imaging using the microscope.

FIG. 8 is a reference image F of the same particles 30 obtained in fluorescence imaging using the microscope 50. Comparing the image C of FIG. 7 with the reference image F of FIG. 8 then shows that the detection of the particles 30 is particularly effective, since substantially the same particles 30 are observed in images C and F.

Figure 9:
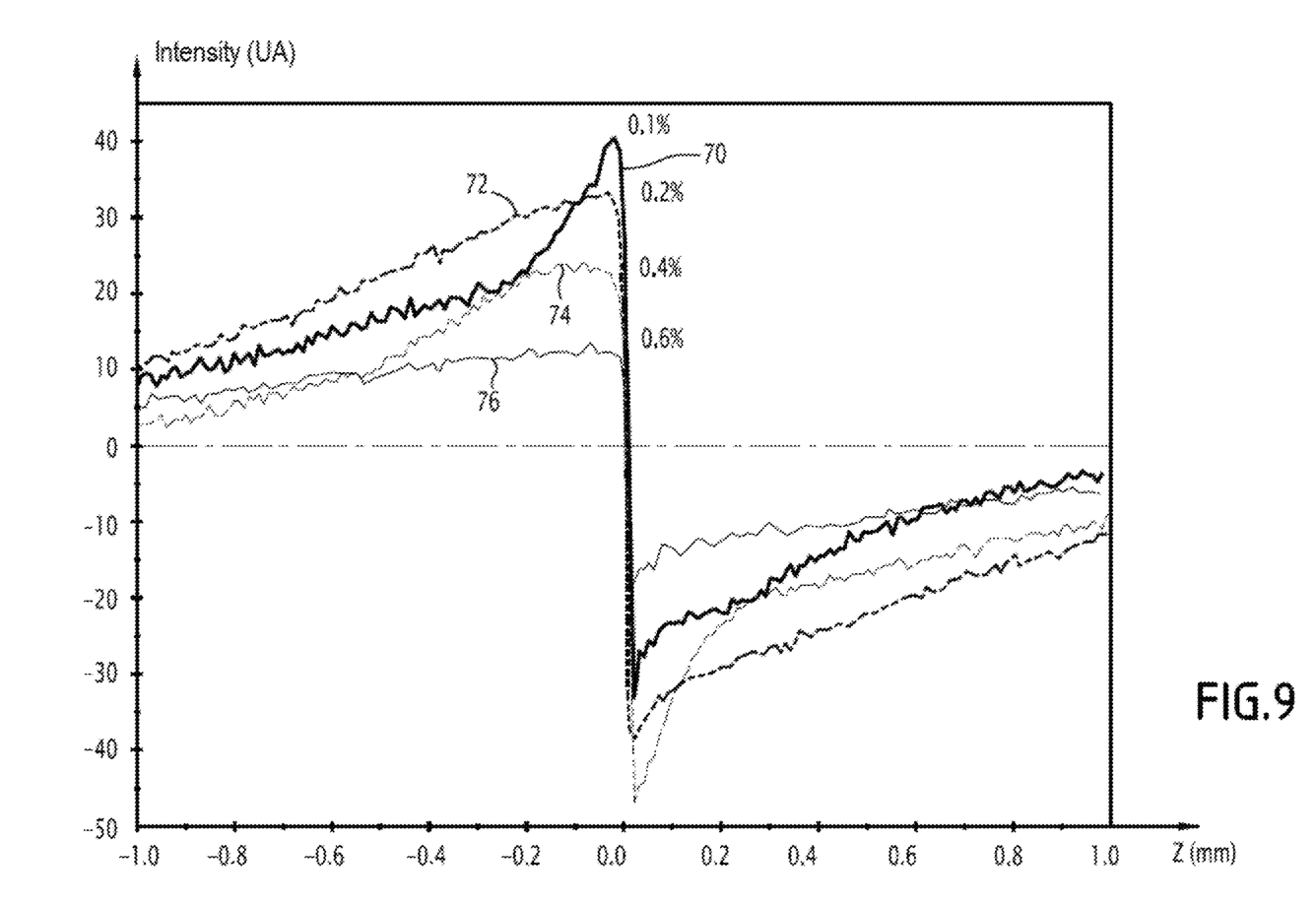
FIG. 9 is a set of curves showing the intensity of the signal acquired by the acquisition device of FIG. 3 for different values of the weight concentration of the PEG 600.

FIG. 9 illustrates different curves 70, 72, 74, 76 representing an intensity profile along the focus axis Z of the acquired image based on the weight concentration of the PEG 600, the weight concentration varying between 0.1% and 0.6%. For each curve 70, 72, 74, 76, the intensity varies based on the focus 26 relative to the main object plane P in the vertical direction Z.

In FIG. 9, a first curve 70 corresponds to a weight concentration of the PEG 600 equal to 0.1%, a second curve 72 corresponds to a weight concentration of the PEG 600 equal to 0.2%, a third curve 74 corresponds to a weight concentration of the PEG 600 equal to 0.4% and a fourth curve 76 corresponds to a weight concentration of the PEG 600 equal to 0.6%.

The four curves 70, 72, 74, 76 show an intensity jump going from dark gray levels to high gray levels, which is characteristic of the presence of a lens, and shows that the wetting film obtained during the evaporation of the drop of the composition 28 forms a micro-lens.

The first curve 70 shows an intensity peak, but that intensity decreases relatively quickly when the focus moves away from the object plane. The second curve 72 has a softer intensity peak, but decreases less quickly.

The best compromise between the intensity and the width of the peak 70, 72, 74 and 76 is obtained for a second curve 72, and the weight concentration of the PEG 600 equal to 0.2% is therefore a preferred value.

Thus, when the hydrophilic polymer is PEG 600, the chosen weight concentration is preferably comprised between 0.2% and 0.8%. It is considered that the film then forms an axicon lens. One skilled in the art will also note that the convexity of the axicon lens depends on the concentration of the hydrophilic polymer.

The advantages of this second embodiment comprise the advantages of the first embodiment previously described.

The second embodiment further has the advantage of improving the signal-to-noise ratio of the acquired image and eliminating certain flaws in the acquired image, due to the acquisition of the first image A for the first focus at $+Z_0$, the acquisition of the second image B for the second focus at $-Z_0$, then the subtraction of the second image B from the first image A, as shown in FIGS. 5 to 7.

In fact, the subtraction of the second image B from the first image A makes it possible to obtain a resulting image C having a better contrast, and that subtraction also makes it possible to eliminate the presence of parasitic elements, such as diffractive particles, dust or micro-drops, found on the slide 26 or on the optical path between the slide 26 and the sensor 34. Such particles form an equivalent signal on the first image A and the second image B. It is then understood that the subtraction of these two images A, B makes it possible to eliminate those particles.

FIGS. 10 to 12 show views similar to those of FIGS. 5 to 7 for another hydrophilic polymer of the composition 28.

In the example embodiment of FIGS. 10 to 12, the hydrophilic polymer is diethylene glycol, denoted DiEG. In other words, the number n of oxyethylene patterns is equal to 2.

Similarly to FIGS. 5 to 7, FIG. 10 shows the first image A obtained for the first focus above the main object plane P, FIG. 11 shows the second image B obtained for the second focus below the main object plane P of the microscope 50, and FIG. 12 shows the resulting image C corresponding to the subtraction of the second image B from the first image A.

Figure 13:
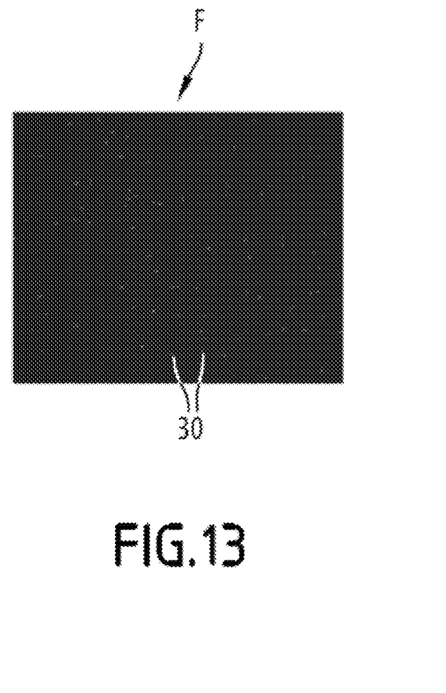
FIG. 13 is a view similar to that of FIG. 8, for the particles detected in FIGS. 10 to 12, FIGS. 14 to 16 are views similar to those of FIGS. 5 to 7, when the polymer contained in the composition is polyethylene glycol with 180 oxyethylene patterns, also called PEG 8000.

FIG. 13 shows the reference image F obtained in fluorescence imaging using the microscope 50 for the same particles 30 as those of FIGS. 10 to 12.

FIGS. 14 to 16 show views similar to that of FIGS. 5 to 7 and those of FIGS. 10 to 12 for another hydrophilic polymer of the composition 28.

In the example embodiment of FIGS. 14 to 16, the hydrophilic polymer is PEG 8000, i.e., polyethylene glycol with the number n of oxyethylene patterns equal to 180.

Similarly to FIGS. 5 to 7 and FIGS. 10 to 12, FIG. 14 shows the first image A, FIG. 15 shows the second image B and FIG. 16 shows the image C resulting from the subtraction of the second image B from the first image A.

Figure 17:
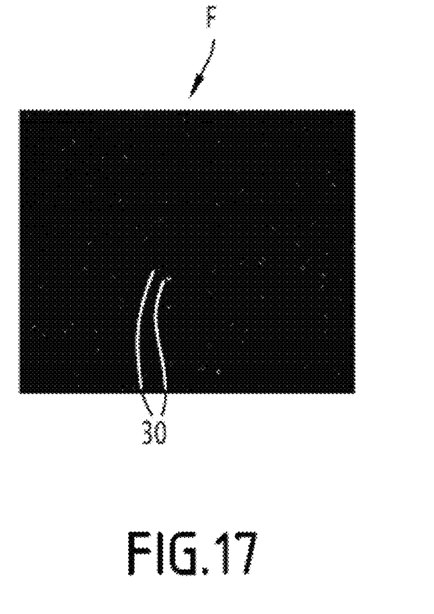
FIG. 17 is a view similar to that of FIG. 8, for the particles detected in FIGS. 14 to 16.

FIG. 17 shows the obtained reference image F, in fluorescence imaging using the microscope 50, for the same particles 30 as those of FIGS. 14 to 16.

The different resulting images C obtained when the hydrophilic polymer is PEG 600, DiEG, or PEG 8000, as shown in FIGS. 7, 12 and 16, show very good optical detection of the particles 30, although they have a very small diameter, such as a diameter equal to 200 nm.

In fact, the comparison of each resulting image C with the corresponding reference image F shows that the detection of the particles 30 is particularly effective, since substantially the same particles 30 are observed each time in images C and F. In other words, the detected particles 30 are substantially the same if we compare FIGS. 7 and 8, FIGS. 12 and 13, respectively, FIGS. 16 and 17, also respectively.

With the composition 28 according to the invention, the drop spreads with the contact angle α of approximately one degree, and the wetting film remains stable for a longer duration than with the composition of the state of the art due to the presence of the hydrophilic polymer.

The adjustment of the weight concentration of the hydrophilic polymer, such as a weight concentration comprised between 0.2% and 0.8% for PEG 600, also makes it possible to improve the signal-to-noise ratio of the image acquired by the acquisition device 24.

Furthermore, the acquisition of the first and second images A, B, then the subtraction of the second image B from the first image A, makes it possible to obtain a resulting image C having a better contrast and to further improve the detection of the particles 30.

The subtraction of the second image B from the first image A also makes it possible to eliminate the presence of parasitic elements, such as diffractive particles, dust or micro-drops, found in the main object plane P.

The detection system 20 according to the invention makes it possible to detect particles having a diameter of approximately 200 nm by lens-free imaging, i.e., with no magnification lens positioned between the light source 22 and the slide 26 or between the slide 26 and the acquisition device 24. Particles with a diameter of approximately 100 nm have also been observed. Such a particle detection is also obtained with no marker, such as fluorescent markers.

The detection system 20 according to the invention is therefore easy to implement and inexpensive, while offering very effective detection of the particles 30.

One can thus see that the optical detection system 20 according to the invention makes it possible to improve the detection of the particles 30 relative to the detection system of the state of the art.

According to another aspect, the invention relates to a composition for optical particle detection, the composition being designed to be arranged on a transparent slide for the acquisition of at least one image of the particles using an optical detection system, the composition comprising water, the particles and a surfactant, the particles having a diameter preferably smaller than 10 μm and in particular a diameter smaller than 1 μm, the surfactant having a concentration preferably at least equal to the critical micellar concentration (CMC), wherein the composition further comprises a hydrophilic polymer, the hydrophilic polymer having a boiling temperature higher than that of water.

Additionally and optionally, the composition comprises one or more of the following features, considered alone or according to any technically possible combinations:

the polymer is a polyethylene glycol defined by the following formula:

where n represents the number of oxyethylene patterns of the polymer;

the number n of oxyethylene patterns is an integer comprised between 2 and 180, preferably comprised between 4 and 16, still more preferably equal to 13;

the number n of oxyethylene patterns is equal to 13, and the hydrophilic polymer has a weight concentration comprised between 0.2% and 0.8%, preferably comprised between 0.4% and 0.6%; and the surfactant comprises polyoxyethylene 20 sorbitan monolaurate.

The invention claimed is:

1. A system for detecting optical particles, the system comprising a transparent slide, a composition arranged on the slide, a light source able to light the composition and the slide, and a device for acquiring at least one image of the composition lit by the light source, the transparent slide being positioned between the light source and the acquisition device, wherein the composition comprises water, the particles, a surfactant and a hydrophilic polymer, the hydrophilic polymer having a boiling temperature higher than that of water.

2. The system according to claim 1, wherein the particles have a diameter smaller than 10 μm.

3. The system according to claim 2, wherein the particles have a diameter smaller than 1 μm.

4. The system according to claim 1, wherein the surfactant has a concentration at least equal to the critical micellar concentration.

5. The system according to claim 1, wherein the polymer is a polyethylene glycol defined by the following formula:

where n represents the number of oxyethylene patterns of the polymer.

6. The system according to claim 5, wherein the number n of oxyethylene patterns is an integer comprised between 2 and 180.

7. The system according to claim 6, wherein the number n of oxyethylene patterns is comprised between 4 and 16.

8. The system according to claim 7, wherein the number n of oxyethylene patterns is equal to 13.

9. The system according to claim 8, wherein the hydrophilic polymer has a weight concentration comprised between 0.2% and 0.8%.

10. The system according to claim 9, wherein the hydrophilic polymer has a weight concentration comprised between 0.4% and 0.6%.

11. The system according to claim 1, wherein the surfactant comprises polyoxyethylene 20 sorbitan monolaurate.

12. A method for detecting optical particles, the method comprising the following steps:

arranging, on a transparent slide, a composition comprising water, the particles and a surfactant, acquiring at least one image of the particles with an optical detection system, wherein the composition further comprises a hydrophilic polymer, the hydrophilic polymer having a boiling temperature higher than that of water.

13. The method according to claim 12, wherein the particles have a diameter smaller than 10 μm.

14. The method according to claim 13, wherein the particles have a diameter smaller than 1 μm.

15. The method according to claim 12, wherein the surfactant has a concentration at least equal to the critical micellar concentration.

16. The method according to claim 12, wherein the polymer is a polyethylene glycol defined by the following formula:

where n represents the number of oxyethylene patterns of the polymer,
the number n of oxyethylene patterns being an integer.

17. The method according to claim 16, wherein the number n of oxyethylene patterns is an integer comprised between 2 and 180.

18. The method according to claim 17, wherein the number n of oxyethylene patterns is comprised between 4 and 16.

19. The method according to claim 18, wherein the number n of oxyethylene patterns is equal to 13.

20. The method according to claim 12, wherein the optical detection system comprises a microscope having a main object plane perpendicular to a vertical direction, and
wherein, during the acquisition step, a first image is acquired for a first focus above the main object plane of the microscope, a second image is acquired for a second focus below the main object plane of the microscope, and the second image is subtracted from the first image.

21. The method according to claim 20, wherein the first focus and the second focus are substantially symmetrical to each other relative to the main object plane of the microscope.

* * * * *